United States Patent
Hadj-Sassi et al.

(10) Patent No.: US 10,472,936 B2
(45) Date of Patent: Nov. 12, 2019

(54) TOTAL GAS IN PLACE ESTIMATE

(71) Applicant: SCHLUMBERGER TECHNOLOGY CORPORATION, Sugar Land, TX (US)

(72) Inventors: Khaled Hadj-Sassi, Muscat (OM); Mohammed Badri, Al-Khobar (SA)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 0 days.

(21) Appl. No.: 16/418,822

(22) Filed: May 21, 2019

(65) Prior Publication Data

US 2019/0271213 A1 Sep. 5, 2019

Related U.S. Application Data

(62) Division of application No. 14/784,729, filed as application No. PCT/US2014/016696 on Feb. 17, 2014, now Pat. No. 10,329,884.

(Continued)

(51) Int. Cl.
*E21B 43/00* (2006.01)
*E21B 49/02* (2006.01)
(Continued)

(52) U.S. Cl.
CPC .............. *E21B 43/00* (2013.01); *E21B 49/02* (2013.01); *G01N 24/081* (2013.01); *G01N 27/02* (2013.01); *G01N 33/246* (2013.01)

(58) Field of Classification Search
CPC .... G01N 33/246; G01N 24/081; G01N 27/02; E21B 43/00; E21B 49/02
See application file for complete search history.

(56) References Cited

U.S. PATENT DOCUMENTS

| | | | | |
|---|---|---|---|---|
| 5,629,623 A | * | 5/1997 | Sezginer | G01N 24/081 324/303 |
| 6,445,187 B1 | * | 9/2002 | Montgomery | G01R 33/02 324/244 |

(Continued)

FOREIGN PATENT DOCUMENTS

WO    WO-2014172002 A1 * 10/2014 ............. E21B 43/00

OTHER PUBLICATIONS

Safton et al., Volumetric and material balance estimation of original raw gas in place: The trouble with Reserve Estimations: A case study of the Alexander Basal Quartz "A" Pool, Alberta. Apr. 2000. (Year: 2000).*

(Continued)

*Primary Examiner* — Jermele M Hollington
*Assistant Examiner* — Sean Curtis (57) ABSTRACT

A mineralogy composition of a formation of interest is determined using core samples or downhole measurements. A dry permittivity is determined for each identified mineral. A volumetric mixing law is employed using the determined mineralogy composition and the determined dry permitivities. An effective matrix permittivity is determined using results from the volumetric mixing law. Dielectric dispersion measurements of the subject formation are acquired using the core samples or the downhole measurements. A dielectric petrophysical model is produced using the dielectric dispersion measurements and the effective matrix permittivity. A water saturation is estimated based on the dielectric petrophysical model. Nuclear magnetic resonance (NMR) T2 measurements having short echo spacings are acquired. A NMR petrophysical model is generated based on the NMR T2 measurements. A total porosity is determined based on the generated NMR petrophysical model. A total (Continued)

gas-in-place estimate is made using the determined total porosity and the estimated water saturation.

6 Claims, 5 Drawing Sheets

Related U.S. Application Data (60) Provisional application No. 61/813,847, filed on Apr. 19, 2013.

(51) Int. Cl.
*G01N 24/08* (2006.01)
*G01N 27/02* (2006.01)
*G01N 33/24* (2006.01)

(56) References Cited

U.S. PATENT DOCUMENTS

| | | | | |
|---|---|---|---|---|
| 7,075,297 | B2* | 7/2006 | Freedman | G01N 24/081 324/303 |
| 7,196,517 | B2* | 3/2007 | Freedman | G01N 24/081 324/303 |
| 8,736,263 | B2* | 5/2014 | Minh | G01N 24/081 324/303 |
| 8,794,318 | B2* | 8/2014 | Harrigan | E21B 49/008 166/100 |
| 8,928,322 | B2* | 1/2015 | Montaron | G01V 5/104 324/324 |
| 9,121,959 | B2* | 9/2015 | Zhang | G01V 5/08 |
| 9,405,036 | B2* | 8/2016 | Kadayam Viswanathan | G01V 3/32 |
| 9,556,720 | B2* | 1/2017 | Onda | E21B 43/26 |
| 9,720,124 | B2* | 8/2017 | Kadayam Viswanathan | G01V 3/32 |
| 9,753,176 | B2* | 9/2017 | Datey | E21B 47/00 |
| 10,241,101 | B2* | 3/2019 | Seleznev | G01N 33/241 |
| 2004/0032257 | A1* | 2/2004 | Freedman | G01N 24/081 324/303 |
| 2004/0055745 | A1* | 3/2004 | Georgi | E21B 49/00 166/250.02 |
| 2007/0244648 | A1* | 10/2007 | Chen | G01N 24/081 702/11 |
| 2012/0043966 | A1* | 2/2012 | Montaron | G01V 5/104 324/324 |
| 2012/0192640 | A1* | 8/2012 | Minh | E21B 7/06 73/152.16 |
| 2013/0113480 | A1* | 5/2013 | Kadayam Viswanathan | G01V 3/32 324/303 |
| 2014/0229112 | A1* | 8/2014 | Datey | E21B 47/00 702/7 |
| 2014/0320126 | A1* | 10/2014 | Heaton | G01V 11/00 324/303 |
| 2015/0127264 | A1* | 5/2015 | Hadj-Sassi | G01V 3/30 702/7 |
| 2016/0047935 | A1* | 2/2016 | Ali | G01V 3/32 702/7 |
| 2016/0061803 | A1* | 3/2016 | Hadj-Sassi | E21B 43/00 324/309 |
| 2016/0097876 | A1* | 4/2016 | Freed | G01V 3/24 703/2 |
| 2016/0186556 | A1* | 6/2016 | Rasmus | G06F 17/11 703/2 |
| 2018/0031732 | A1* | 2/2018 | Mosse | G01V 99/005 |
| 2018/0203151 | A1* | 7/2018 | Kouchmeshky | G01V 3/38 |
| 2018/0321412 | A1* | 11/2018 | Wang | G01V 3/20 |
| 2019/0094405 | A1* | 3/2019 | Itskovich | G01V 3/28 |

OTHER PUBLICATIONS

Pirrone et al., An innovative dielectric dispersion measurement for better evaluation of thin layered reservoirs applied in a south italy well. Mar. 2011—10th Offshore Mediterranean Conference and Exhibition in Ravenna, Italy. (Year: 2011).*

Hemingway, James. Dieletric Dispersion Logging—A New Petrophysical Measurement for the Permian Basin, 2011 Schlumberger. (Year: 2011).*

Verma, Mahendra. Calculation of Hydrocarbon-in-place in gas and gas-condensate reservoirs—carbon dioxide sequestration. 2012— US Geological Survey (USGS). (Year: 2012).*

Kouchmeshky et al., Using Dielectric Dispersion Logging to Calculate the Paramaters of Archie's Law. Copyright Jan. 2016— Society of Petroleum Engineers. (Year: 2016).*

Seleznev et al., Application of dielectric dispersion logging to oil-shale reservoirs. SPWLA 52nd Annual Logging Symposium, May 2011. (Year: 2011).*

Written Opinion of International Search Authority—PCT/US2014/ 016696, dated May 2014 (Year: 2014).*

* cited by examiner

TOTAL GAS IN PLACE ESTIMATE

CROSS-REFERENCE TO RELATED APPLICATIONS

This patent application is a divisional application of U.S. patent application Ser. No. 14/784,729, filed Feb. 17, 2014, which is hereby incorporated herein by reference in its entirety.

BACKGROUND

Shale gas reservoir characterization is important for accurate estimation of the original gas-in-place, the production rates, and the storage capacity of depleted reservoirs. Characterization typically includes laboratory measurements of pore, water, and gas volumes, and sorption capacity of selected shale samples. Conventional methods of sampling and measuring these properties have had limited success due to the tight and multiscale nature of the core samples. Shales commonly have relatively low porosity and ultra-low permeability. In addition, they have pores with a wide range of sizes, which often leads to multimodal pore size distribution. The latter is associated with the diversity of minerals that comprise shale, such as clays, carbonates, and organic material (e.g., kerogen). The complexity in mineral content leads to fundamental questions, and often uncertainties, relating to the calculation of the petrophysical properties, the total amounts and spatial distribution of original fluids in the reservoir, their thermodynamic states (i.e., adsorbed or free), and, finally, the mechanisms of their transport under the reservoir conditions.

A dielectric logging device may be used to measure the formation dielectric constant and conductivity at multiple frequencies from 20 MHz to 1 GHz. One such device features a short, articulated pad, allowing optimal pad contact even in rough boreholes and minimization of environmental effects. Mudcake or other material directly in front of the pad is measured using two transmitters and eight receivers which are mounted on the pad, in addition to a pair of electric dipoles operating in reflection mode. The analysis of the multifrequency dielectric measurements provides information about formation water content, water salinity, and rock texture.

Numerous dielectric forward models have been developed and used to convert the dielectric measurements into water saturation, water salinity, and rock matrix. Certain models are generally known as a bimodal model, a Stroud-Milton-De (SMD) model, a shaly sand model, and a complex refractive index model (CRIM). Each of those models has inherent strengths and weaknesses based on the assumptions intrinsic to the particular model. Some model types (e.g., effective medium and phenomenological) work well with different rock types, taking into account the order and shape of replacement material. Other model types (e.g., empirical and semi-empirical) can accurately predict values for the data used to construct them, but are not widely applicable to data sets consisting of different mineralogies, porosities, or water saturations. The CRIM, for example, falls within this latter category, as it does not account for micro-geometry of the rock components, and does not account for electrochemical interaction between the components.

SUMMARY

A mineralogy composition of a formation of interest is determined on core samples or downhole formation using spectroscopy measurements. A dry permittivity is determined for each identified mineral. A volumetric mixing law is employed using the determined mineralogy composition and the determined dry permitivities. An effective matrix permittivity is determined using results from the volumetric mixing law. Dielectric dispersion measurements of the subject formation are acquired on the core samples using the dielectric spectrometer or across the formation of interest using the downhole measurements. A dielectric petrophysical model is produced using the dielectric dispersion measurements and the effective matrix permittivity. A water saturation is estimated based on the dielectric petrophysical model. Nuclear magnetic resonance (NMR) T2 measurements having short echo spacings are acquired. A NMR petrophysical model is generated based on the NMR T2 measurements. A total porosity is determined based on the generated NMR petrophysical model. A total gas-in-place estimate is made using the determined total porosity and the estimated water saturation.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. Embodiments are described with reference to the following figures. The same numbers are generally used throughout the figures to reference like features and components.

DETAILED DESCRIPTION

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Figure 1:
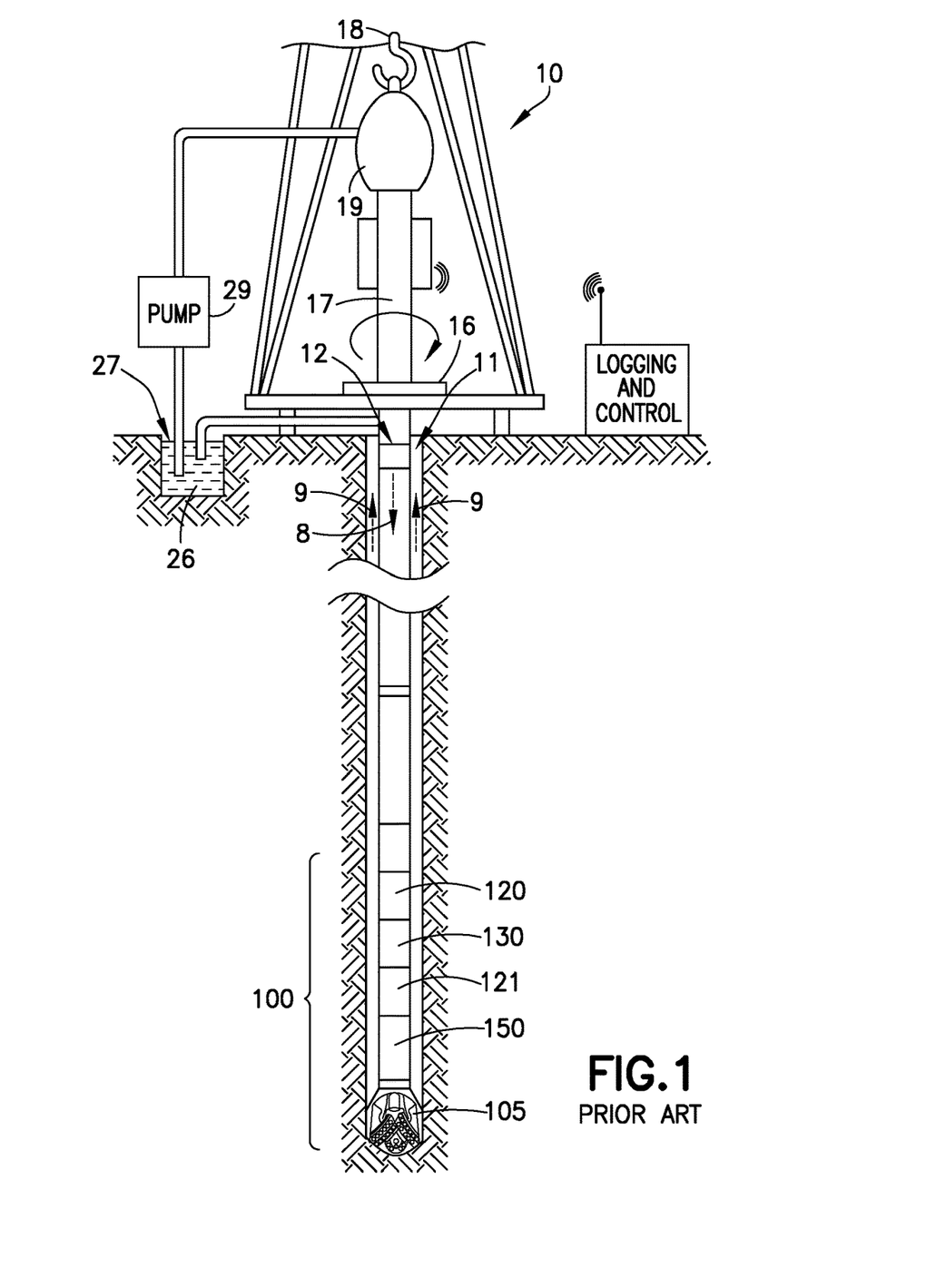
FIG. 1 illustrates a prior art well site system.

FIG. 1 illustrates a well site system in which various embodiments can be employed. The well site can be onshore or offshore. In this example system, a borehole 11 is formed in subsurface formations by rotary drilling in a manner that is well known. Some embodiments can also use directional drilling, as will be described hereinafter.

A drill string 12 is suspended within the borehole 11 and has a bottom hole assembly 100 which includes a drill bit 105 at its lower end. The surface system includes platform and derrick assembly 10 positioned over the borehole 11, the assembly 10 including a rotary table 16, kelly 17, hook 18 and rotary swivel 19. The drill string 12 is rotated by the rotary table 16, energized by means not shown, which engages the kelly 17 at the upper end of the drill string. The drill string 12 is suspended from a hook 18, attached to a traveling block (also not shown), through the kelly 17 and a rotary swivel 19 which permits rotation of the drill string relative to the hook. As is well known, a top drive system could be used.

In the example of this embodiment, the surface system further includes drilling fluid or mud 26 stored in a pit 27 formed at the well site. A pump 29 delivers the drilling fluid 26 to the interior of the drill string 12 via a port in the swivel 19, causing the drilling fluid to flow downwardly through the drill string 12 as indicated by the directional arrow 8. The drilling fluid exits the drill string 12 via ports in the drill bit 105, and then circulates upwardly through the annulus region between the outside of the drill string and the wall of the borehole, as indicated by the directional arrows 9. In this well known manner, the drilling fluid lubricates the drill bit 105 and carries formation cuttings up to the surface as it is returned to the pit 27 for recirculation.

The bottom hole assembly 100 of the illustrated embodiment includes a logging-while-drilling (LWD) module 120 and a measuring-while-drilling (MWD) module 130. It may also include a roto-steerable system and motor 150 and drill bit 105.

The LWD module 120 is housed in a special type of drill collar, as is known in the art, and can contain one or a plurality of known types of logging tools. It will also be understood that more than one LWD and/or MWD module can be employed, e.g. as represented at 121. (References, throughout, to a module at the position of 120 can also mean a module at the position of 121 as well.) The LWD module includes capabilities for measuring, processing, and storing information, as well as for communicating with the surface equipment. In the present embodiment, the LWD module includes a resistivity measuring device.

The MWD module 130 is also housed in a special type of drill collar, as is known in the art, and can contain one or more devices for measuring characteristics of the drill string and drill bit. The MWD tool further includes an apparatus (not shown) for generating electrical power to the downhole system. This may typically include a mud turbine generator powered by the flow of the drilling fluid, it being understood that other power and/or battery systems may be employed. In the present embodiment, the MWD module includes one or more of the following types of measuring devices: a weight-on-bit measuring device, a torque measuring device, a vibration measuring device, a shock measuring device, a stick/slip measuring device, a direction measuring device, and an inclination measuring device.

Figure 2:
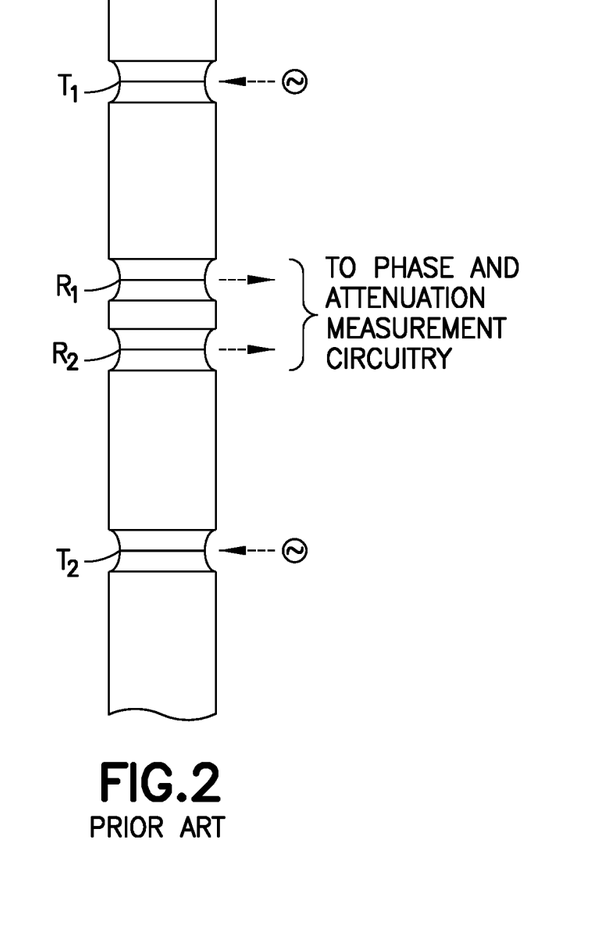
FIG. 2 shows a prior art logging tool.

An example of a tool which can be the LWD tool 120, or can be a part of an LWD tool suite 121, is shown in FIG. 2. As seen in FIG. 2, upper and lower transmitting antennas, $T_1$ and $T_2$, have upper and lower receiving antennas, $R_1$ and $R_2$, therebetween. The antennas are formed in recesses in a modified drill collar and mounted in MC or insulating material. The phase shift of the electromagnetic wave between the receivers provides an indication of formation resistivity at a relatively shallow depth of investigation, and the attenuation of the electromagnetic wave between the receivers provides an indication of formation resistivity at a relatively deep depth of investigation. U.S. Pat. No. 4,899,112 can be referred to for further details. In operation, attenuation-representative signals and phase-representative signals are coupled to a processor, an output of which is coupleable to a telemetry circuit.

Some electromagnetic (EM) logging tools use one or more tilted or transverse antennas, with or without axial antennas. Those antennas may be transmitters or receivers. A tilted antenna is one whose dipole moment is neither parallel nor perpendicular to the longitudinal axis of the tool. A transverse antenna is one whose dipole moment is perpendicular to the longitudinal axis of the tool, and an axial antenna is one whose dipole moment is parallel to the longitudinal axis of the tool. A triaxial antenna is one in which three antennas (i.e., antenna coils) are arranged to be mutually orthogonal. Often one antenna (coil) is axial and the other two are transverse. Two antennas are said to have equal angles if their dipole moment vectors intersect the tool's longitudinal axis at the same angle. For example, two tilted antennas have the same tilt angle if their dipole moment vectors, having their tails conceptually fixed to a point on the tool's longitudinal axis, lie on the surface of a right circular cone centered on the tool's longitudinal axis and having its vertex at that reference point. Transverse antennas obviously have equal angles of 90 degrees, and that is true regardless of their azimuthal orientations relative to the tool.

Some embodiments will now be described with reference to the figures. Like elements in the various figures may be referenced with like numbers for consistency. In the following description, numerous details are set forth to provide an understanding of various embodiments and/or features. However, it will be understood by those skilled in the art that some embodiments may be practiced without many of these details and that numerous variations or modifications from the described embodiments are possible. As used here, the terms "above" and "below", "up" and "down", "upper" and "lower", "upwardly" and "downwardly", and other like terms indicating relative positions above or below a given point or element are used in this description to more clearly describe certain embodiments. However, when applied to equipment and methods for use in wells that are deviated or horizontal, such terms may refer to a left to right, right to left, or diagonal relationship, as appropriate. It will also be understood that, although the terms first, second, etc. may be used herein to describe various elements, these elements should not be limited by these terms. These terms are only used to distinguish one element from another.

The terminology used in the description herein is for the purpose of describing particular embodiments only and is not intended to be limiting. As used in the description and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

A system and method to estimate the total gas in place in a shale reservoir are disclosed. The disclosed system and method may be used in conjunction with a computing system as described below. In one embodiment, measurements or determinations of dielectric dispersion, nuclear magnetic resonance, and mineralogy composition (e.g., geochemical measurements) are used to estimate the total gas in place.

Figure 3:
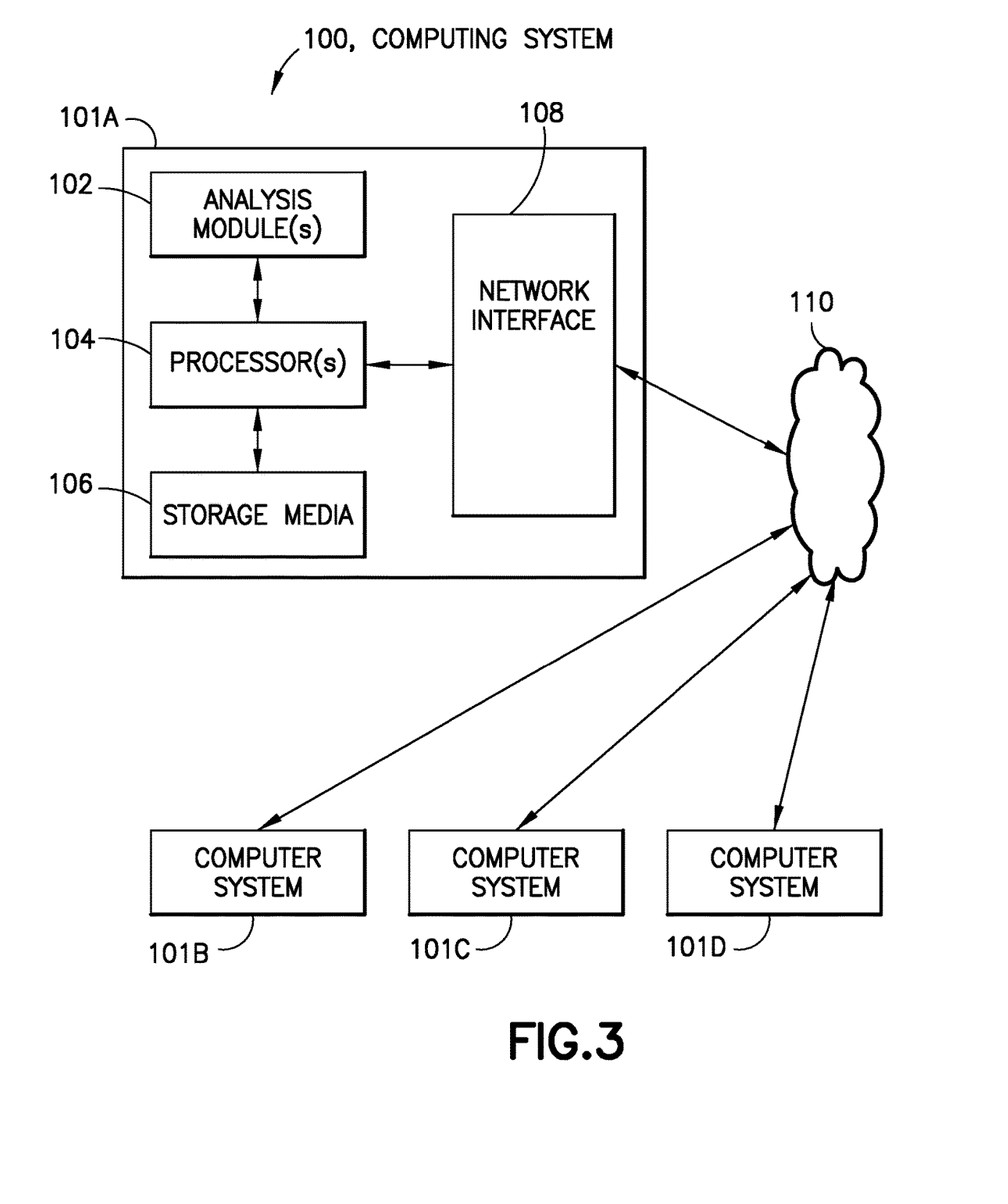
FIG. 3 illustrates an example computing system usable for one or more disclosed embodiments, in accordance with the present disclosure.

The computing system 100 shown in FIG. 3 can be an individual computer system 101A or an arrangement of distributed computer systems. The computer system 101A includes one or more analysis modules 102 that are configured to perform various tasks according to some embodiments, such as one or more methods disclosed herein (e.g., any of the steps, methods, techniques, and/or processes, and/or combinations and/or variations and/or equivalents thereof). To perform those various tasks, analysis module 102 operates independently or in coordination with one or more processors 104 that is (or are) connected to one or more storage media 106. The processor(s) 104 is (or are) also connected to a network interface 108 to allow the computer system 101A to communicate over a data network 110 with one or more additional computer systems and/or computing systems, such as 101B, 101C, and/or 101D (note that computer systems 101B, 101C, and/or 101D may or may not share the same architecture as computer system 101A, and may be located in different physical locations, e.g. computer systems 101A and 101B may be on a ship underway on the ocean, while in communication with one or more computer systems such as 101C and/or 101D that are located in one or more data centers onshore, on other ships, and/or located in various countries on different continents).

A processor can include a microprocessor, microcontroller, processor module or subsystem, programmable integrated circuit, programmable gate array, or another control or computing device.

The storage media 106 can be implemented as one or more computer-readable or machine-readable storage media. Note that while in the example embodiment of FIG. 3 storage media 106 is depicted as within computer system 101A, in some embodiments, storage media 106 may be distributed within and/or across multiple internal and/or external enclosures of computing system 101A and/or additional computing systems. Storage media 106 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the instructions discussed above can be provided on one computer-readable or machine-readable storage medium, or can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

It should be appreciated that computing system 100 is only one example of a computing system, and that computing system 100 may have more or fewer components than shown, may combine additional components not depicted in the example embodiment of FIG. 3, and/or computing system 100 may have a different configuration or arrangement of the components depicted in FIG. 3. For example, though not shown explicitly, computing system 100 would generally include input and output devices such as a keyboard, a mouse, a display monitor, and a printer and/or plotter. The various components shown in FIG. 3 may be implemented in hardware, software, or a combination of both hardware and software, including one or more signal processing and/or application specific integrated circuits.

Further, the steps in the processing methods described above may be implemented by running one or more functional modules in information processing apparatus such as general purpose processors or application specific chips, such as ASICs, FPGAs, PLDs, or other appropriate devices. These modules, combinations of these modules, and/or their combination with general hardware are all included within the scope of this disclosure.

For definiteness and ease of discussion of the subject matter disclosed herein, a bimodal model was used for the processing and interpretation of obtained dielectric experimental data. It can be summarized by the following equation: $\varphi_w = f(\in, \in_m, \in_w, \in_h, \text{texture})$ where $\varphi_w$ is the water volume fraction, $\varphi$ is the total porosity, and texture represents the grain shape/fraction and the pore structure. $\in$ is the measured complex permittivity, and $\in_m, \in_w, \in_h$ are, respectively, the permittivities of the matrix, water, and hydrocarbons.

As shown in the functional relation above, the matrix permittivity, along with the dielectric measurements, is used to estimate the water-filled porosity. The estimated water volume depends on the permittivity of the rock matrix. The matrix permittivity of shales can vary from approximately 4.9 to 7 because of the different mineral types constituting the rock. In contrast to carbonates and sandstone rocks in which only a few minerals are present, shale rocks are characterized by the diversity of their mineral types, and each mineral has its own permittivity value. Sensitivity analysis demonstrates that a one-unit error of matrix permittivity (i.e., the difference between $\in_m=5$ and $\in_m=6$) could propagate to an approximately 2 p.u. variation of estimated water-filled porosity, a huge error for the low porosity rocks of less than 10 p.u. total porosity.

Combining the dielectric dispersion measurements, the nuclear magnetic resonance (NMR) responses, and the mineralogy composition of the formation enhances the estimation of the total gas in place of the shale gas formation. In certain embodiments, a method is disclosed to determine the dielectric permittivity of each mineral in a shale gas rock, including pyrite, which can affect the dielectric responses. Accurate estimation of the volume of pyrite provides for enhanced interpretation of the dielectric dispersion.

Figure 4:
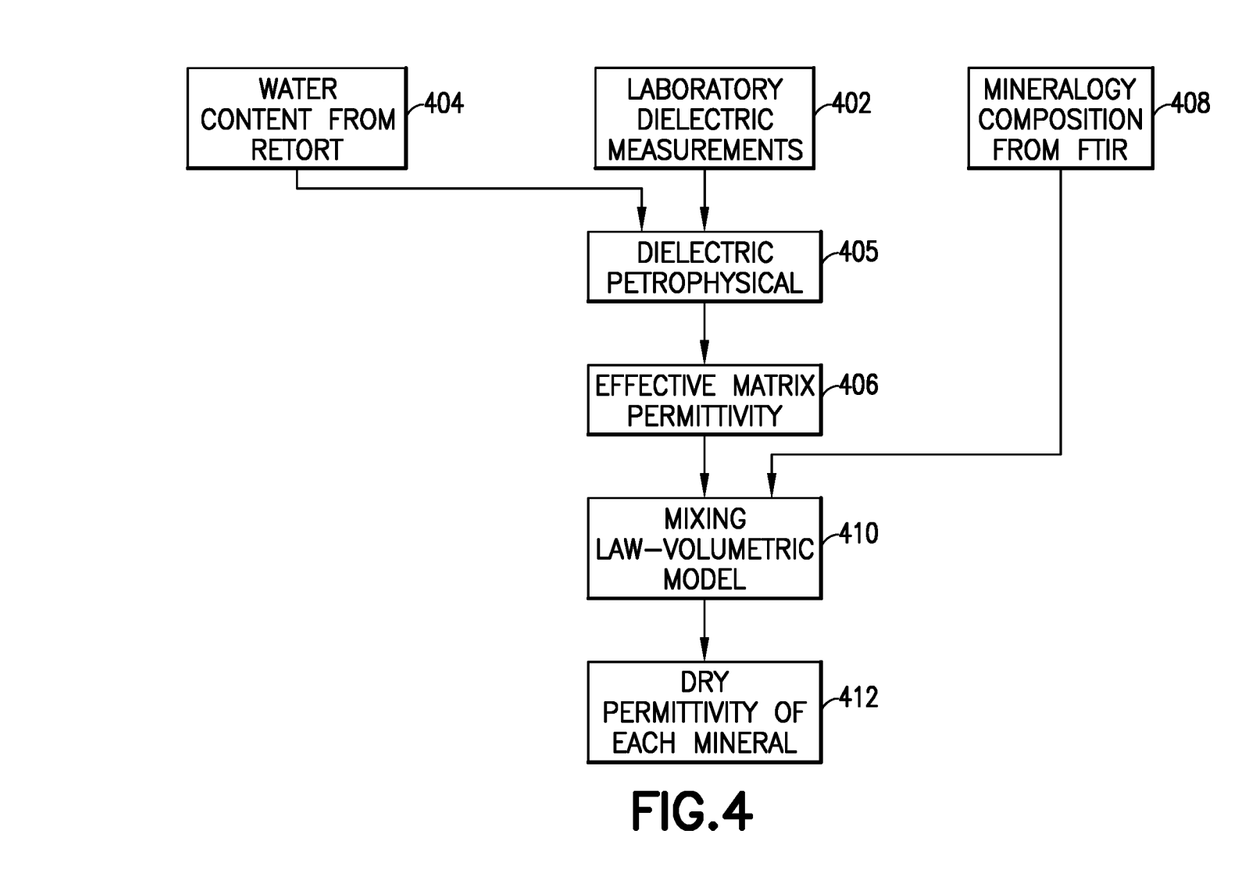
FIG. 4 is a flow chart for at least one workflow embodiment used to estimate the dry permittivity of each mineral of a sample of shale gas rocks, in accordance with the present disclosure.

Mineralogy is identified and quantified using one or more laboratory techniques, such as the dual range Fourier transform infrared (FTIR) technique or X-ray diffraction (XRD). FIG. 4 depicts a flowchart of one embodiment of the subject disclosure. This embodiment allows one to accurately estimate the effective permittivity of the rock using the mineralogy composition details. That is, an estimate of the dry permittivity of each mineral of a sample of shale gas rock may be applied to estimate the effective matrix permittivity. The effective matrix permittivity of each rock sample is estimated by inverting the measured permittivity and conductivity dispersions on selected shale gas samples. In at least certain embodiments, the laboratory dielectric measuring device used comprises a network analyzer (NA) which is controlled using a computer module. The network analyzer is calibrated using a set of short, open, and 50-ohm standards. The rock samples may be ground flat on each end to fit into the flat dielectric coaxial cell. The complex dielectric permittivity is commonly expressed as $$\epsilon = \epsilon_r + i\frac{\sigma}{\omega \epsilon_0}$$

where $\epsilon_r$ is the relative dielectric permittivity or the dielectric constant and is the real part of the complex permittivity. The imaginary part relates to the high-frequency conductivity ($\sigma$) of the sample, the free-space permittivity ($\epsilon_0$), and the angular frequency ($\omega$). As the frequency of the measurement increases, the term $$\frac{\sigma}{\omega \epsilon_0}$$

decreases, and the dielectric constant $\epsilon_r$ starts to play an increasing role.

The dielectric physics model inverts the dielectric constant and conductivity dispersions into an effective permittivity of the rock matrix. The water content is an input parameter in this inversion method. The water content is measured from a high-resolution retort technique (e.g., using a distillation unit) on crushed samples. The inverted effective permittivity and the mineralogy composition measured by FTIR (or XRD) system are used to estimate the dry permittivity of each mineral.

A deterministic misfit data approach was developed to compute the dry permittivity of the rock minerals. To reconstruct the effective matrix permittivity estimated above, a least squares technique is used to minimize the distance between the estimated $\epsilon_{meff}$ and the computed matrix permittivity value. The forward model used to predict $\epsilon_m$ during the inversion process is the complex refractive index (CRI) dielectric mixing law expressed as $$\sqrt{\epsilon_{meff}} = \sum_{i=1}^{n} V_i \sqrt{\epsilon_i},$$

where $V_i$ represent the volume fraction of rock minerals, $\epsilon_i$ is the dry matrix permittivity of each mineral, and n is the number of minerals measured by the FTIR system. In at least certain embodiments, the L2 norm function includes a data misfit function and a regularization term. The weight of each function during the inversion process is controlled by a trade-off parameter $\alpha$. The L2-norm regularization part includes a reference dry permittivity value $\epsilon_{ref}$ of each mineral. This is used to constrain unreasonable values and guide the inversion process to achieve reasonable permittivity values of minerals. The function to be minimized is then expressed by the following equation:

$$J = \frac{1}{2}\left\|\sqrt{\epsilon_{meff}} - \sum_{i=1}^{n} V_i \sqrt{\epsilon_i}\right\|^2 + \frac{1}{2}\sum_{i=1}^{n} \alpha_i \left\|\sqrt{\epsilon_i} - \sqrt{\epsilon_{ref}}\right\|^2$$

The dry permittivity values determined from this method include many of the minerals and organic materials constituting the shale gas rocks, including pyrite, which is a relatively heavy mineral in shale gas rocks. Pyrite influences the formation evaluation when it is present in large quantities. As alluded to above, pyrite generally affects the dielectric responses, enhancing the conductivity and permittivity, particularly in dry samples. Therefore, an accurate estimation of the dry permittivity of pyrite is important so that it can be accounted for in the interpretation of dielectric responses. The analyzed samples may contain a broad range of pyrite.

Figure 5:
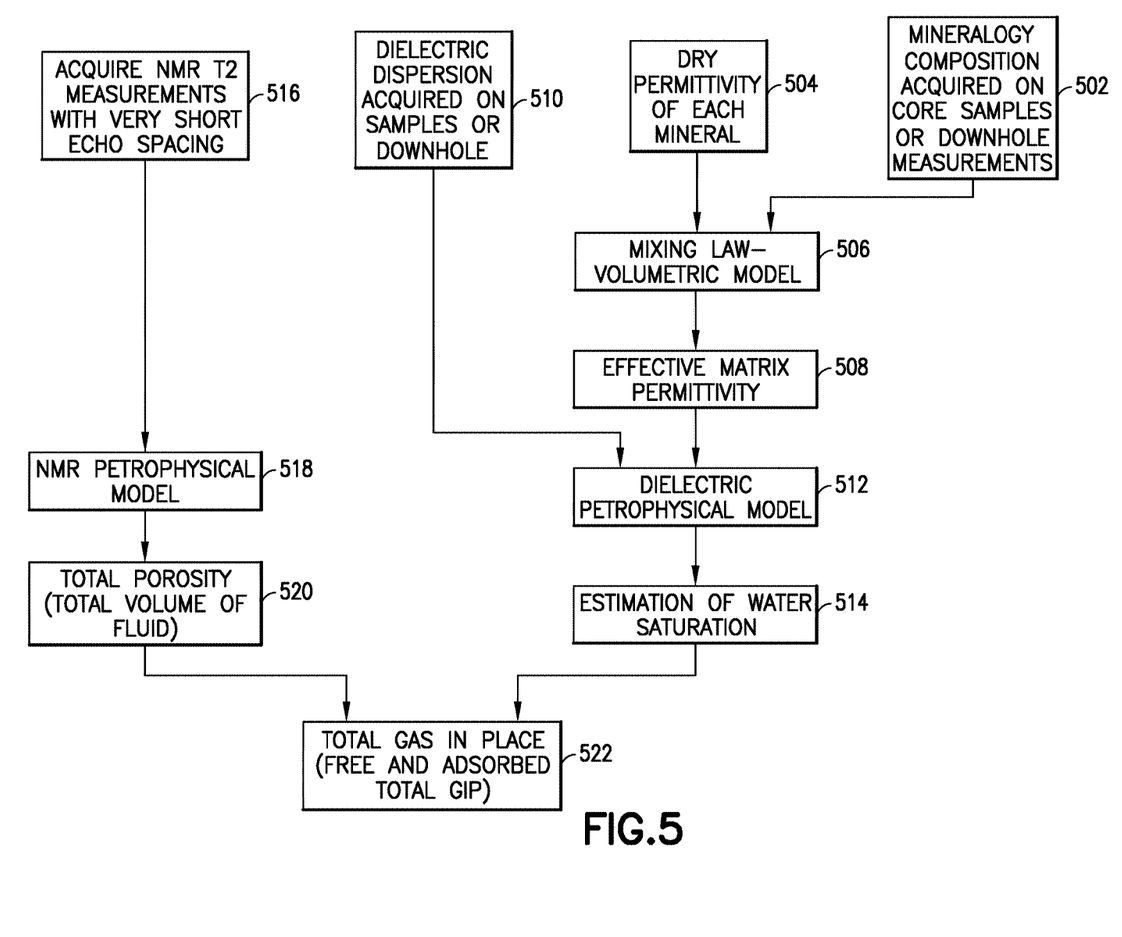
FIG. 5 is a flow chart for at least one workflow embodiment used to estimate the total gas in place of a sample of shale gas rocks, in accordance with the present disclosure.

The dielectric dispersion and NMR measurements may be combined to accurately estimate the total gas in place. The determined permittivity of the rock minerals allows one to accurately compute the effective permittivity of the rock matrix. This effective permittivity value may then be used to accurately estimate the water volume fraction using the dielectric dispersion. An NMR signal with short echo spacing provides for a total volume of fluid present within the multi-modal pores down to the nanometer scale. The difference between the total fluid from NMR and the total water content determined from the dielectric measurements provides an accurate estimate of total gas in place (free and adsorbed). FIG. 5 shows a flowchart of an embodiment that could be applied to the laboratory data acquired on core samples and logging data acquired downhole.

Specifically, in particular embodiments, combining the dielectric dispersion and NMR measurements to estimate the total gas in place expect an accurate estimation of total porosity from NMR T2 distribution, in addition to a precise quantification of the water content from the dielectric measurements. The dry permittivity of the minerals estimated from the previous method (e.g., see FIG. 4) is used to accurately compute the effective matrix permittivity of shale gas rocks. This careful determination of the matrix permittivity value is used with the dielectric dispersion to accurately estimate the water saturation from the measured permittivity and conductivity (e.g., see FIG. 5). Note that the water saturation determined from the dielectric measurements is the sum of the free, capillary, and bound clay water and structural water. If one wishes to measure the pore systems from the NMR T2 data, very short echo spacing is required. For example, a 0.130 msec echo spacing may be selected for proper characterization of shale samples with pore sizes at the nanometer scale. In non-limiting examples, shorter echo spacing may be better if the hardware and software tool allow. This very short echo spacing measures the micro and nano-porosity, hence provides a better estimation of the total porosity of the shale gas rocks. The NMR T2 measurement provides the total volume of the fluid present in the rock, such as the capillary bound water, free water, clay bound water, free gas, and adsorbed gas, etc. Therefore, the subtraction of the water volume estimated from the dielectric measurements from the total fluid volume from NMR T2 measurements provides an accurate estimation of gas in place of the studied formation. This technique, again, is illustrated in FIG. 5, and may be applied to either a laboratory study on core samples or with field data obtained from downhole acquisitions.

Attention is now directed to processing procedures, methods, techniques, and workflows that are in accordance with some embodiments. Some operations in the processing procedures, methods, techniques, and workflows disclosed herein may be combined and/or the order of some operations may be changed. It is important to recognize that geologic interpretations, sets of assumptions, and/or domain models such as velocity models may be refined in an iterative fashion. This concept is applicable to the processing procedures, methods, techniques, and workflows discussed herein. This iterative refinement can include use of feedback loops executed on an algorithmic basis, such as at a computing device (e.g., computing system 100, FIG. 3), and/or through manual control by a user who may make determinations regarding whether a given step, action, template, or model has become sufficiently accurate for the evaluation of the subsurface three-dimensional geologic formation under consideration.

As stated above, FIG. 4 shows a flowchart illustrating an embodiment in accordance with this disclosure. In this embodiment, the workflow comprises conducting dielectric dispersion measurements on core samples from a formation of interest (402). Pieces are cut from the core samples and the water content is determined using one or more of the available laboratory methods (e.g., a high resolution retort method or a thermo-gravimetric analysis method) (404). Those data are used to determine the dielectric petrophysical properties of the samples (405), and the effective permittivity of the matrix of the selected rock is estimated from those determined dielectric petrophysical properties (406). That is, the determined water content is used along with the obtained dielectric measurement to invert for the effective permittivity of the rock matrix. The mineralogy composition (i.e., estimated weight percent) of the sample may be determined using a known laboratory method (e.g., FTIR or XRD) (408). The determined effective matrix permittivity is used with the estimated weight percent of different minerals in a mixing law to perform a volumetric analysis (410). A deterministic approach may be used for the inversion process. A forward model may be, for example, the complex refractive index mixing law. The dry permittivity of each mineral may be estimated (412).

As stated above, FIG. 5 shows a flowchart illustrating another embodiment in accordance with this disclosure. In this embodiment, the workflow comprises determining the mineralogy composition of the subject formation using core samples or downhole measurements (502). The dry permittivity of each mineral is determined or estimated (504). The mineralogy composition and the determined dry permitivities are input into a volumetric mixing law (506) and that is used to determine an effective matrix permittivity (508). The dielectric dispersion of the subject formation is determined using core samples or downhole measurements (510). The determined dielectric dispersion and the effective matrix permittivity are used to produce a dielectric petrophysical model (512). An estimation of water saturation may be made based on the dielectric petrophysical model (514). In addition, NMR T2 measurements with very short echo spacing may be acquired (516); a NMR petrophysical model may be generated (518); and a total porosity (i.e., total volume of fluid) may be determined based on the NMR measurements (520). An estimate of the total gas-in-place (free and adsorbed) may be made using the total porosity determined from the NMR measurements and the estimated water saturation from the dielectric petrophysical model (522).

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the scope of the present disclosure, and that they may make various changes, substitutions, and alterations herein without departing from the scope of the present disclosure.

The Abstract at the end of this disclosure is provided to comply with 37 C.F.R. § 1.72(b) to allow the reader to quickly ascertain the nature of the technical disclosure. It is submitted with the understanding that it will not be used to interpret or limit the scope or meaning of the claims.

While only certain embodiments have been set forth, alternatives and modifications will be apparent from the above description to those skilled in the art. These and other alternatives are considered equivalents and within the scope of this disclosure and the appended claims. Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method, comprising:
obtaining dielectric dispersion measurements on core samples having matrix material from a formation of interest;
determining a water content of the core samples by analyzing at least a portion of the core samples;
determining dielectric petrophysical properties of the core samples using the determined water content and the dielectric dispersion measurements;
estimating an effective matrix permittivity of the core sample matrix material using the determined dielectric petrophysical properties;
determining a mineralogy composition of the core sample by analyzing at least a portion of the core samples;
employing a volumetric mixing law using the determined effective matrix permittivity and the determined mineralogy composition; and determining a dry permittivity for each mineral identified by the volumetric mixing law.

2. The method of claim 1, wherein the dielectric dispersion measurements are made using a network analyzer.

3. The method of claim 1, wherein the determining a water content comprises using a retort technique or a thermo-gravimetric technique.

4. The method of claim 1, wherein the estimating an effective matrix permittivity comprises inverting measured permittivity and conductivity dispersions.

5. The method of claim 1, wherein the determining a mineralogy composition comprises using a Fourier transform infrared technique or an X-ray diffraction technique.

6. The method of claim 1, wherein the employing a volumetric mixing law comprises using a complex refractive index technique.

* * * * *